(12) United States Patent
Groenland et al.

(10) Patent No.: US 10,293,165 B2
(45) Date of Patent: May 21, 2019

(54) ELECTRICAL MULTICHANNEL SYSTEM, PARTICULARLY FOR NEURAL STIMULATION

(71) Applicant: KONINKLIJKE PHILIPS N.V., Eindhoven (NL)

(72) Inventors: Alfons Wouter Groenland, Valkenswaard (NL); Ke Wang, Valkenswaard (NL)

(73) Assignee: Koninklijke Philips N.V., Eindhoven (NL)

(*) Notice: Subject to any disclaimer, the term of this patent is extended or adjusted under 35 U.S.C. 154(b) by 778 days.

(21) Appl. No.: 14/441,273

(22) PCT Filed: Nov. 4, 2013

(86) PCT No.: PCT/IB2013/059883
§ 371 (c)(1),
(2) Date: May 7, 2015

(87) PCT Pub. No.: WO2014/083454
PCT Pub. Date: Jun. 5, 2014

(65) Prior Publication Data
US 2015/0306393 A1    Oct. 29, 2015

Related U.S. Application Data

(60) Provisional application No. 61/730,153, filed on Nov. 27, 2012.

(51) Int. Cl.
*A61N 1/36* (2006.01)
*A61N 1/375* (2006.01)
(Continued)

(52) U.S. Cl.
CPC ...... *A61N 1/36125* (2013.01); *A61B 5/04001* (2013.01); *A61N 1/0488* (2013.01);
(Continued)

(58) Field of Classification Search
CPC .................................................. A61N 1/375
See application file for complete search history.

(56) References Cited

U.S. PATENT DOCUMENTS 5,324,322 A    6/1994   Grill et al.
7,286,878 B2   10/2007  Stypulkowski
(Continued)

FOREIGN PATENT DOCUMENTS

WO    2011105664 A1    9/2011

OTHER PUBLICATIONS

Heuvelman, W.M. et al. "TiN reactive sputter deposition studied as a function of the pumping speed", Thin Solid Films 332 (1998), 335-339.
(Continued)

*Primary Examiner* — Carl H Layno
*Assistant Examiner* — Jennifer L Ghand

(57) ABSTRACT

The invention relates to an electrical multichannel system (100) and to a neural stimulation and/or recording device comprising such a system. The multichannel system comprises a plurality of application components (130), e.g. stimulation electrodes, and associated access points (120) that are connected by a plurality of electrical lines (110). The resistances of these lines are adjusted to given target values, for example to equal values, by incorporating appropriate tuning sections (140) into the electrical lines. The lines may for example comprise different geometries and/or materials in the tuning sections.

15 Claims, 6 Drawing Sheets

(51) Int. Cl.
*A61N 1/04* (2006.01)
*A61N 1/05* (2006.01)
*A61B 5/04* (2006.01)

(52) U.S. Cl.
CPC ......... *A61N 1/0534* (2013.01); *A61N 1/0541* (2013.01); *A61N 1/0543* (2013.01); *A61N 1/0551* (2013.01); *A61N 1/375* (2013.01)

(56) References Cited

U.S. PATENT DOCUMENTS

| | | |
|---|---|---|
| 8,688,231 B2 | 4/2014 | Decre et al. |
| 8,731,673 B2 | 5/2014 | Vetter et al. |
| 2003/0088302 A1* | 5/2003 | Shirakawa ............... A61N 1/05 607/122 |
| 2005/0222656 A1 | 10/2005 | Wahlstrand et al. |
| 2008/0140195 A1 | 6/2008 | Su et al. |
| 2008/0208283 A1* | 8/2008 | Vetter .................. A61N 1/0539 607/45 |
| 2011/0224765 A1 | 9/2011 | Harberts et al. |
| 2012/0112869 A1 | 5/2012 | Nishikawa et al. |
| 2012/0271386 A1 | 10/2012 | Li et al. |
| 2013/0282090 A1 | 10/2013 | Decre et al. |

OTHER PUBLICATIONS

Schroder, R.K., "Semiconductor material and device characterization", 3rd ed, IEEE press, Wiley Interscience, ISBM 978-0-471-73906-7, p. 11.

* cited by examiner

ELECTRICAL MULTICHANNEL SYSTEM, PARTICULARLY FOR NEURAL STIMULATION

CROSS-REFERENCE TO PRIOR APPLICATIONS

This application is the U.S. National Phase application under 35 U.S.C. § 371 of International Application Serial No. PCT/IB2013/059883, filed on Nov. 4, 2013, which claims the benefit of U.S. Application Ser. No. 61/730,153, filed on Nov. 27, 2012. These applications are hereby incorporated by reference herein.

FIELD OF THE INVENTION

The invention relates to an electrical multichannel system comprising a multichannel track that connects application components to access points. In particular, it relates to a neural stimulation and/or recording device, for instance a hearing implant, a visual implant, or a deep brain stimulation (DBS) system.

BACKGROUND OF THE INVENTION

The patent document WO 200809298 A2 discloses a system for deep brain stimulation comprising an electrode array at the end of a carrier with conductive interconnects to connect the electrodes to external components. The line width of the conductive interconnects shall be adjusted to equalize the resistance across all leads in view of their different lengths.

SUMMARY OF THE INVENTION

In view of the state of the art, it would be advantageous to have means that allow for a more simple and flexible design of multichannel systems like neural implants.

This concern is addressed by an electrical multichannel system according to claims 1 and 5, and a neural stimulation and/or recording device according to claim 15. Preferred embodiments are disclosed in the dependent claims.

According to a first aspect, the invention relates to an electrical multichannel system, i.e. a system carrying electrical signals and/or electrical energy (as voltages, currents, charges, or the like) along a plurality of "channels" (or routes, lines, leads etc.). The system comprises the following components:

a) A plurality of "application components" and associated "access points".

b) A multichannel track with a plurality of electrical lines, each line connecting one of the aforementioned application components to one access point with a predetermined value for the electrical resistance ("target resistance") of said line. Moreover, each line shall comprise a "tuning-section" defined by the following features:

- The tuning-section extends between a starting-point and an end-point (said points being part of the considered line).
- The spatial distance between said starting-point and said end-point is the same for all lines.
- The (electrical) resistivity and the cross-section are substantially the same for all lines at their starting-points.
- The resistivity and the cross-section are substantially the same for all lines at their end-points.
- The resistances between starting-point and end-point differ between at least one first line and one second line.

The term "application component" shall refer to an arbitrary component, device, or system that shall receive input from and/or deliver input to an electrical line of the multichannel track. An example of an "application component" is an electrode for stimulating neural tissue and/or for recording electrical signals from such tissue.

The term "access point" shall refer to an arbitrary component, device, or system via which input intended for an application component can be delivered to an electrical line and/or via which output coming from an application component can be received from such a line. In a typical example, the "access point" is a bond pad where external circuits can be connected to a line of a multichannel track.

The term "multichannel track" shall in general denote the set of all electrical lines connecting the application components one-to-one to the access points. Typically, the multichannel track will at least partially be cable-like, with electrical lines running close and parallel to each other.

The target resistances may in general assume any value of the (ohmic) resistance prescribed by design. In a preferred embodiment, the target resistances may be the same for all lines, thus allowing to transmit electrical signals across each line in a similar way.

The described electrical multichannel system has the advantage that given target values for the total resistances of the lines can be met irrespective of differences that may exist between the lines, particularly irrespective of different line lengths. This is because the resistance of the tuning sections can be adapted accordingly, i.e. be set to a value such that the overall resistance of the whole line meets the given target value.

In the following, various preferred embodiments of the invention will be described in more detail.

According to one embodiment of the multichannel system, the geometries of the first line and the second line differ in the tuning sections. The first and the second lines may for instance have different lengths in their tuning sections (while the lengths of the tuning sections, i.e. the distances between starting-points and end-points, are the same). The course of the first line may for example be straight from the starting-point to the end-point, while the course of the second line is a meander of greater length and hence higher resistance.

Additionally or alternatively, the first and the second lines may have different cross sections within their tuning sections (wherein the line with the smaller cross section will produce a higher resistance if the resistivities are equal). Lines with a rectangular cross section may for example differ in their width and/or thickness to produce such a difference in cross section.

Moreover, the first line and/or the second line may be split into parallel lines within the associated tuning section. If both lines are split, the lengths of the parallel sections may be different, yielding different total resistances.

According to another embodiment, the first line may comprise in the tuning section a subsection that is composed of at least two different materials. A composition of several materials can be used to tune the resistance of the first line, for instance by choosing different relative fractions of said materials and/or by extending the subsection of several materials over different fractions of the tuning section. The at least two materials may be mixed homogeneously (e.g. as an alloy of two metals), or they may be arranged inhomogeneously (e.g. as two spatially separated blocks).

In a preferred example of the aforementioned embodiment, both the first line and the second line comprise in their tuning sections subsections composed of at least two materials (e.g. of gold and platinum), wherein said subsections extend over different fractions of the respective lengths of the tuning sections.

In another embodiment, the first line and the second line have non-matching courses of resistivities along their tuning sections. In this context, the resistivity of a line at some point shall be defined as the average of the resistivity of said line over the cross section of said line at the considered point (wherein the cross section is taken perpendicular to the flow of electrical signals through the line). Based on this definition, the "course of resistivity" can be defined as the resistivity as a function of position along the considered line. For example, if the resistivity of a line is constant throughout the tuning section, the "course of resistivity" will be a line parallel to the x-axis denoting the position x along said line; if the resistivity increases from starting-point to end-point, the "course of resistivity" will be an ascending curve, and so on. The two courses of resistivity of the first line and the second line are considered to be "non-matching" if they cannot be brought to a complete overlap (choosing the orientation of the x-axes in the tuning sections appropriately). A simple example is again if the first and the second lines have different resistivities that are constant throughout their tuning sections.

In another embodiment of the invention, the above comparison of courses of resistivities is extended from tuning sections to complete lines. More particularly, the invention relates according to a second aspect to an electrical multichannel system comprising:

a) A plurality of application components and associated access points.

b) A multichannel track with a plurality of electrical lines, each line connecting one application component to one access point with a given target resistance.

Furthermore, the multichannel track shall comprise at least one first line and one second line with the following features:

The first line is not longer than the second line (with other words: it is shorter or of equal length).

The first line and the second line have non-matching courses of resistivity over the extension of the first line.

In this multichannel system, desired target values in total resistance of the lines are met by designing the lines with appropriate courses of resistivity. In contrast to the previous embodiment, these different courses of resistivities are typically not restricted to limited (tuning-) sections, but extend over the complete lines (wherein two resistivities of lines of different lengths can of course only be compared over the extension of the smaller length; exemplary cases are illustrated in FIG. 13).

In the following, various embodiments of the invention will be described that relate to the multichannel systems according to the first and/or the second aspect.

In one such embodiment, the first line comprises a subsection with a resistivity different from any of the resistivities occurring in the second line, or vice versa. This is one particular way of designing non-matching courses of resistivity (within a tuning section or across the whole extension of the shorter line): One of the lines is built to have at (least locally) a resistivity that occurs nowhere in the other line.

In a particular example of the aforementioned embodiment, the first and second lines have different resistivities that are constant along their extensions and/or along their tuning sections (if present). The first and the second line may for example (completely or in the tuning section) consist of different materials with different resistivities.

According to another embodiment, the first and the second lines comprise subsections with differently doped substrates. These subsections may extend over the whole length of the corresponding lines or be restricted to their tuning sections (if present). Doping substrates differently is one possible way to adjust the resistivities of the lines as desired.

In still another embodiment, the first and the second lines may comprise subsections with different fractions of silicides. As in aforementioned embodiment, the corresponding variations in chemical composition can be used to generate desired courses of resistivity.

In many applications of the present invention, the first and the second lines will have different total lengths or at least different lengths outside the tuning sections (if present). This may for example be due to the need to connect spatially distributed application components and access points that require connections of different lengths. Moreover, the lines of a multichannel track may have different lengths due to their manufacturing procedure. In wafer based processes, due to the limitation by (e.g. circular shaped) substrate size, such multichannel tracks are for instance often produced by curved structures on a foil, yielding different lengths of lines at the inner and at the outer radius of the curve, respectively.

In general, the target resistances of the lines of the multichannel track can have any value that is desired in the application at hand. In a practically important case, the target resistances of all lines are equal to each other, thus equalizing the electrical channel properties between access points and application components. In case of the aforementioned differences in the lengths of different lines, the aim of equal target resistances can only be met by additional effort, particularly by the above described means. For instance, the resistance of the lines in the tuning sections can be chosen to compensate for undesired differences in resistance occurring outside the tuning sections.

It was already mentioned that the lines of the multichannel track may run along curved parallel paths. In this case, differences in length between inner and outer lines of said paths can be compensated for by the means of the present invention.

Of course there may be many other sources for (undesired) resistance variations between lines of a multichannel track. Resistance differences may for example be induced by a spatial distribution of application components and access points. Moreover, resistance spread of straight lines can occur as result of process spread along the substrate, affecting for example the metal thickness or the resistivity. A spread in resistivity may be due to stoichiometry variations, occurring for example in reactively sputtered TiN ($Ti_xN_y$ with x≠y). The sensitivity of the stoichiometry and hence resistivity for deposition parameters has been described in literature (W. M. Heuvelman et al., "TiN reactive sputter deposition studied as a function of the pumping speed", Thin Solid Films 332 (1998), 335-339, Elsevier), and may also happen on wafer level due to inhomogeneous plasmas. Often the spread is well known and quantified and hence can be compensated for.

According to another embodiment, the lines of the multichannel track are at least partially realized as thin-film conductors. This is for example the case in neural stimulation or recording applications in which small, flexible electrodes or probes have to be inserted into neural tissue.

The invention further relates to a neural stimulation and/or recording device, particularly to a hearing implant (or cochlear implant), a visual implant, or a deep brain stimulation system, said device comprising an electrical multichannel system of the kind described above. The "application components" of such a device will typically be electrodes, and the "access points" will typically be bond pads or the like.

BRIEF DESCRIPTION OF THE DRAWINGS

These and other aspects of the invention will be apparent from and elucidated with reference to the embodiments described hereinafter.

In the drawings.

Like reference numbers refer in the Figures to identical or similar components.

DETAILED DESCRIPTION OF EMBODIMENTS

Implantable neurostimulation devices have been used for decades to treat acute or chronic neurological conditions. Deep brain stimulation (DBS), the mild electrical stimulation of sub-cortical structures, belongs to this category of implantable devices, and has been shown to be therapeutically effective for Parkinson's disease, Dystonia, and Tremor. New applications of DBS in the domain of psychiatric disorders (obsessive compulsive disorder, depression) are being researched and show promising results. In typical systems, probes of about 1.2 mm-diameter and 10-50 cm length are connected to an Implantable Pulse Generator (IPG). There is a need for more and smaller electrodes in order to better control the delivery of electrical stimulation, because current stimulation causes mild to severe side-effects in about 30% of the patients.

Magnetic resonance (MR) safety of these implantable devices is an important issue. MR safety, reduction of the heating of the implant as a result of the electrical field during MR scanning, can be realized by winding of the cable wires on the device (cf. WO2010055453A1). However, the winding substantially increases the length of the cable wiring.

A DBS lead can be manufactured by winding a thin film around a core. These thin films are typically produced on a carrier wafer (or plate) and released from the wafer (or plate) after manufacturing. In the case of a DBS lead that is manufactured with wound thin film, the length of the thin film is substantial and can exceed the size of the carrier substrate. Therefore, the cable is often designed as a spiral; multiple spirals are placed on a single wafer allowing simultaneous fabrication of more than one thin film in a single fabrication process. This is described for example in patent document WO 2012069649 A1.

Figure 1:
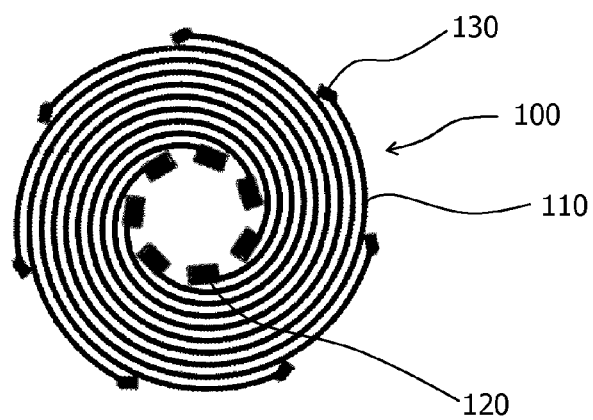
FIG. 1 shows a top view onto seven multichannel systems of a deep brain stimulation (DBS) system disposed as interlaced spirals on a carrier.

FIG. 1 shows a top view onto a plurality of seven such cables (or "multichannel systems") 100 that are arranged as interlaced spirals on a single carrier.

Figure 2:
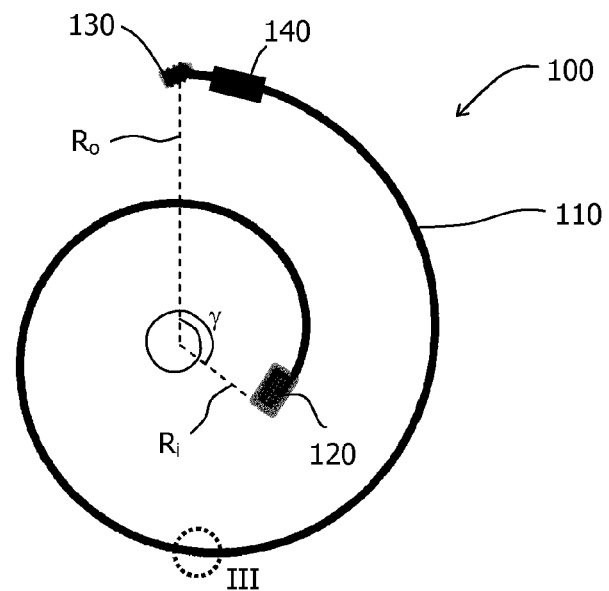
FIG. 2 depicts a single multichannel system of FIG. 1 separately.
Figure 4:
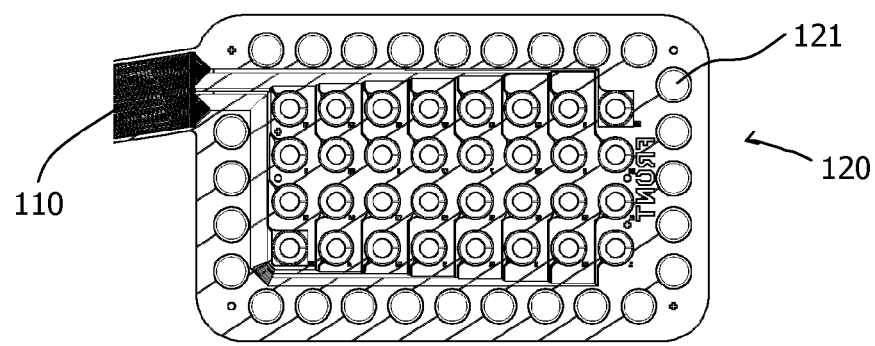
FIG. 4 shows an enlarged representation of the bond pads (access points) of the multichannel system of FIG. 2.

FIG. 2 shows separately a single spiral or multichannel system 100 which consists mainly of three components:

A plurality 120 of "access points", which is shown in more detail in FIG. 4. In this example, the access points are bond pads 121 distributed in a rectangular array.

Figure 3:
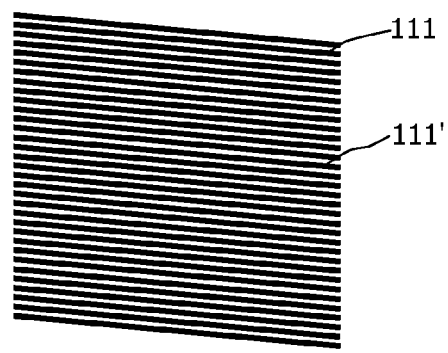
FIG. 3 shows the detail III of FIG. 2.

A multichannel track 110 comprising a plurality of (e.g. 32) electrical lines running parallel to each other on a spiral path. FIG. 3 is an enlarged view of the detail III of FIG. 2 and shows the parallel lines 111, 111', . . . .

Figure 5:
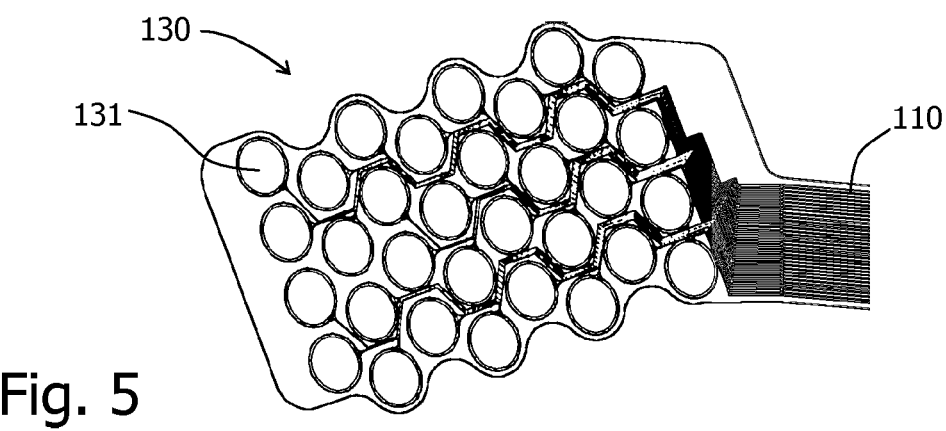
FIG. 5 shows an enlarged representation of the electrodes (as application components) of the multichannel system of FIG. 2.

A plurality 130 of "application components", which is shown in more detail in FIG. 5. In this example, the application components are electrodes 131 for a stimulation of neural tissue that are distributed in an array.

Each single line 111, 111' of the multichannel track 110 connects one of the electrodes 131 to just one access point 121. The access points can then further be connected to the outputs of an IPG (not shown) or the like.

The geometry of the spiral 110 is defined by an outer radius $R_o$ (e.g. about 62 mm), an inner radius $R_i$ (e.g. about 24 mm), and the angle $\varphi$ over which $R_o$ linearly decreases to $R_i$. The electrical lines that lie at the outer edge of the spiral 110 will be longer than the lines at the inner edge. For a line width of about 40 µm, the difference in length between inner and outer lines will be about 12 mm, resulting in a resistance difference of about 3.65%.

As can be seen from FIGS. 4 and 5, the connection wires between the spiral part of the multichannel track 110 and the actual electrodes 131 and bond pads 121, respectively, have different lengths and accordingly different resistances. These differences add to the total spread in resistances of the electrical lines of the multichannel track 110.

The electrical resistance between the access points 121 and the electrodes 131 is preferably designed to be equal for all electrodes. This allows for example to use a single pulse generator in the IPG that is multiplexed to all electrodes. Any inequality in connection resistance would lead to increased complexity in the pulse generator design, by means of for instance the addition of (tunable) matching filters or multiple pulse generators.

As explained above, the track resistance R will however in practice not be equal for all lines 111, 111'. In a spiral cable design with equally spaced tracks with equal width, the outer tracks have a longer length than the tracks towards the centre of the spiral.

As the resistance is directly proportional to the length (at constant track width), this length difference leads to a difference in track resistance R. Moreover, the spirally shaped cable is connected to the electrodes 131 in the distal end and to the bond pads 121 in the proximal end with (low width, hence relatively high Ohmic) wire pieces that are different for each track. Also these wire pieces lead to an additional component in the spread of the track resistance R.

Figure 6:
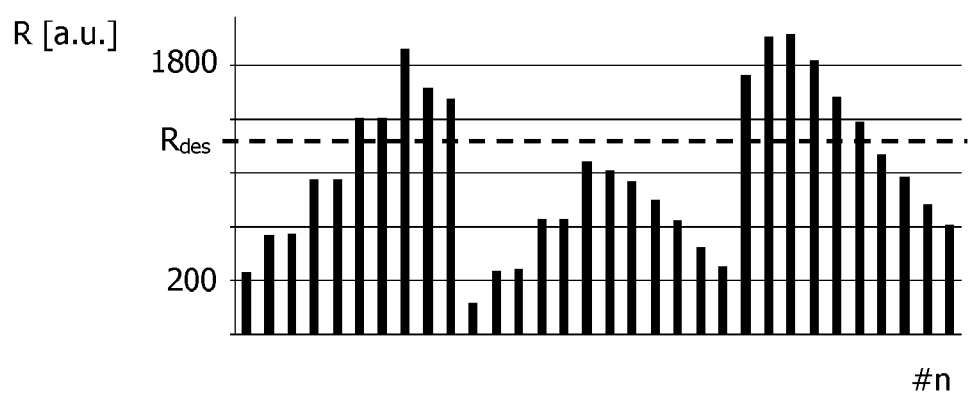
FIG. 6 is a diagram showing the difference in resistance of the electrical lines of the multichannel system of FIG. 2.

This situation is illustrated in FIG. 6, which is a diagram showing the track resistances R (arbitrary units) originating from the resistance difference in distal and proximal end (not spiral cable) for single lines of equal width of a standard multichannel track.

As a solution, it is proposed here to take particular measures that make the total resistances of all lines in the multichannel track 110 between the electrodes 131 and the bond pads 121 (or IPG) equal, corresponding for example to a common value $R_{des}$. In order to explain how this is achieved, the characteristic electrical parameters are first defined with reference to FIG. 7.

Figure 7:
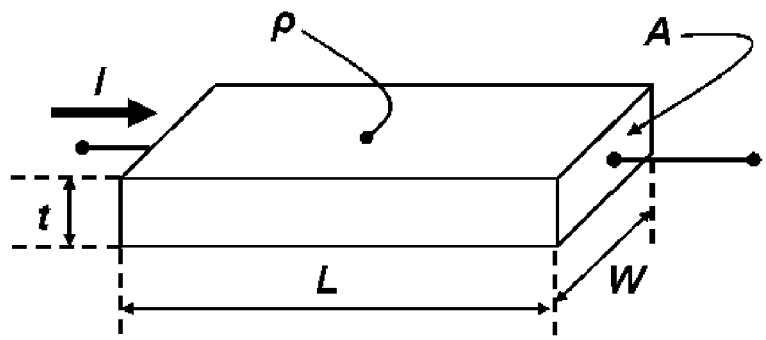
FIG. 7 illustrates the definition of electrical parameters for a slab of material.

The resistance of a slab of material as shown in FIG. 7 is given by the formula $$R = \rho \frac{L}{Wt} = \rho \frac{L}{A}$$

with R being the resistance (in Ω), ρ the resistivity (Ω·cm), L the length (cm), W the width (cm), t the thickness (cm), and A=Wt the area through which the current I flows (cf. D. K. Schroder, "Semiconductor material and device characterization", $3^{rd}$ ed, IEEE press, Wiley Interscience, ISBN 978-0-471-73906-7, page 11). The resistivity is a material parameter and gives the inability of the material to conduct electrical current.

Figure 8:
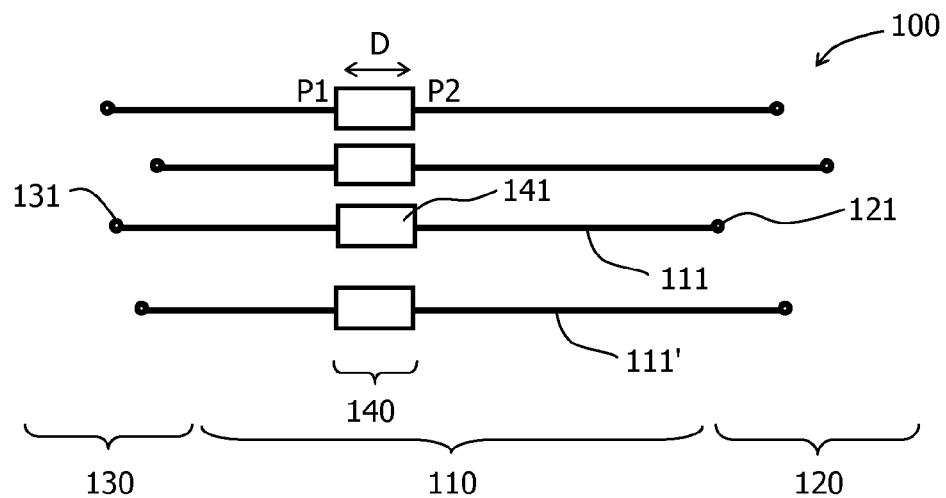
FIG. 8 shows schematically the incorporation of tuning sections into electrical lines of different lengths.

FIG. 8 schematically illustrates the multichannel system 100 of FIGS. 1-5 and a solution approach of the present invention. As discussed above, the multichannel system 100 consists of a plurality 120 of access points 121 that are connected to a plurality 130 of application components 131 via a multichannel track 110 with a plurality of individual lines 111, 111', . . . . The Figure also illustrates that these electrical lines 111, 111' may have different lengths (and may additionally have varying resistivities along their extensions, see below).

In order to compensate for the resistance spread that is caused by the different lengths of the lines, it is proposed to incorporate a set 140 of tuning sections 141 into the electrical lines 111, 111', wherein each tuning section 141 comprises means to compensate for the resistance variation in the path outside the section.

More particularly, a tuning section 141 shall extend between a starting-point P1 and an end-point P2 (wherein these two points are functionally equivalent, i.e. their names can be interchanged) that are the same distance D apart for all tuning sections 141. Furthermore, it is assumed that the resistivity ρ and cross section A of all lines are substantially the same at the starting-points P1 of their tuning sections 141. Similarly, the resistivity ρ and cross section A of all lines shall substantially be the same at the end-points P2 of their tuning sections 141 (wherein resistivity and/or cross section of a line at the starting point P1 may be different from that at the end-point P2). Typically, the resistivity and/or cross sections of the lines will be constant throughout the whole extension of said lines left and/or right from the tuning sections 141.

In the following, various possibilities to adjust a desired resistance within the tuning sections will be described in more detail.

Figure 9:
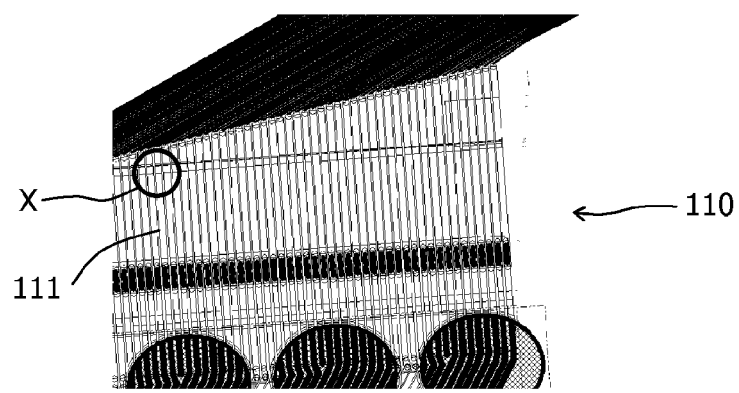
FIG. 9 shows a detail of a multichannel track of a DBS system.
Figure 10:
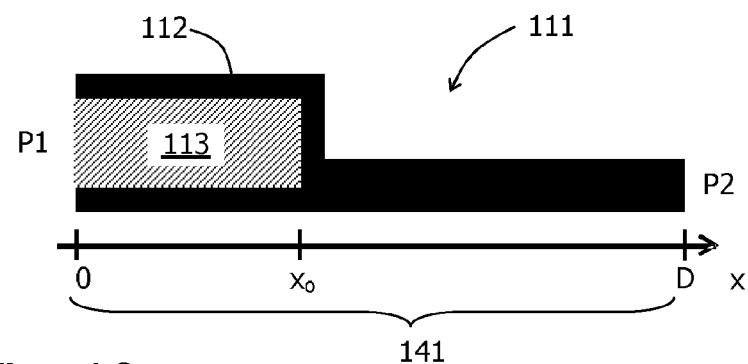
FIG. 10 shows a cross section through a line in the area X of FIG. 9.

FIG. 9 shows a part of a multichannel track 110 of a DBS system; a longitudinal section through one line 111 at detail X is further represented in FIG. 10. It can be seen that this line 111 is composed of two materials, namely a kernel 113 of gold (Au, having a typical thickness about 2.5 μm) that is packed within layers 112 of platinum (Pt). The kernel material 113 extends only over a fraction ($x_0$/D) of the axial length D. If materials with a high difference in resistivity (or layers with a high difference in "sheet resistance" ρ/t) are used, as in the example of Au and Pt, the whole resistance between the left starting-point P1 and the right end-point P2 of the considered tuning section 141 can be adjusted as desired.

An adaptation of (local or global) resistivity is also possible for a single conductive layer. In case of (poly) silicon conductors, the doping can for example be varied locally by adjusting the implantation dose. Moreover, silicide tracks can be formed by in situ reaction of silicon with a metal to form Metal-silicon eutectics, wherein the degree of silicidation is designed by the amount of metal present (metal layer thickness) or by local (self) heating to different temperatures (cf. EP20100010930).

Figure 11:
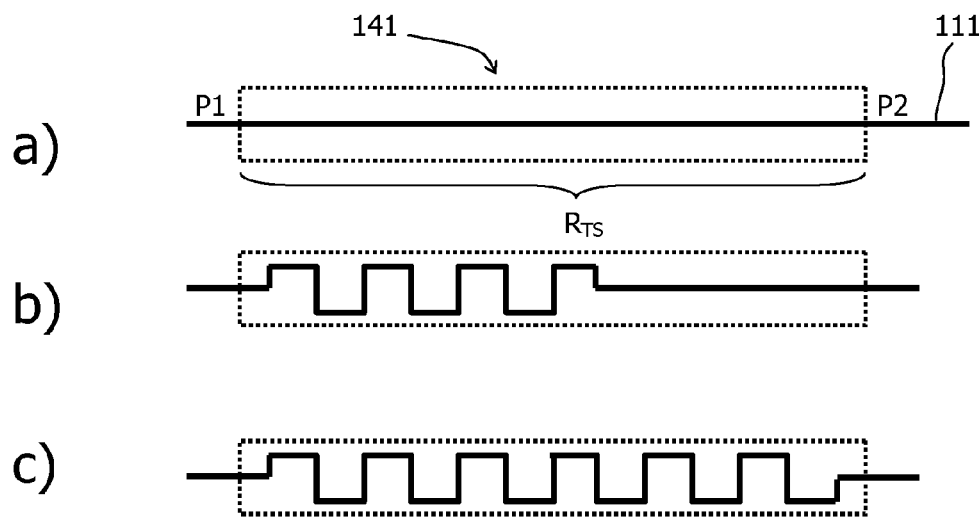
FIG. 11 shows different tuning sections with (a) a straight line, (b) a short meander, and (c) a long meander of the electrical line.

FIG. 11 illustrates another way for establishing different resistivities in a tuning section 141. In this case, the length of the current path within the tuning section 141 is varied. The Figure illustrates three exemplary cases:

a) A straight connection between the starting point P1 and the end-point P2, yielding a low resistance.

b) A short meandering subsection between starting point P1 and end-point P2, yielding an intermediate resistance.

c) A long meandering subsection between starting point P1 and end-point P2, yielding a high resistance.

Figure 12:
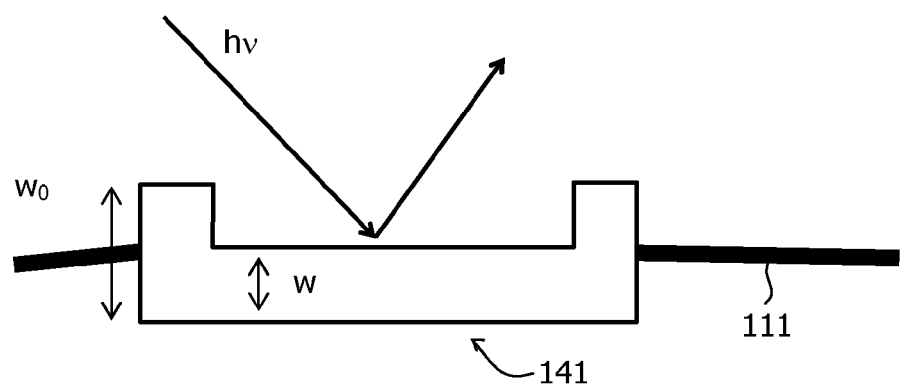
FIG. 12 illustrates the laser trimming of a tuning section (cross section)

FIG. 12 illustrates a manufacturing procedure to adapt the resistance of a tuning section 141. In this case the width of the tuning section, which is originally chosen to have a high value $w_0$, is reduced to a desired value w for example by laser ablation. An alternative way would be to produce the width w by design already.

A similar approach can be used to adjust the thickness of a tuning section. This can for example be done by the removal of material by plasma or wet chemical etching (where the entire substrate is protected from etching by masking materials, with only desired areas exposed), by focused ion beam processing or by laser trimming. Alternatively, it is also possible to selectively add material to increase a layer thickness. This may for instance be achieved by focused ion beam assisted chemical vapor deposition.

Figure 13:
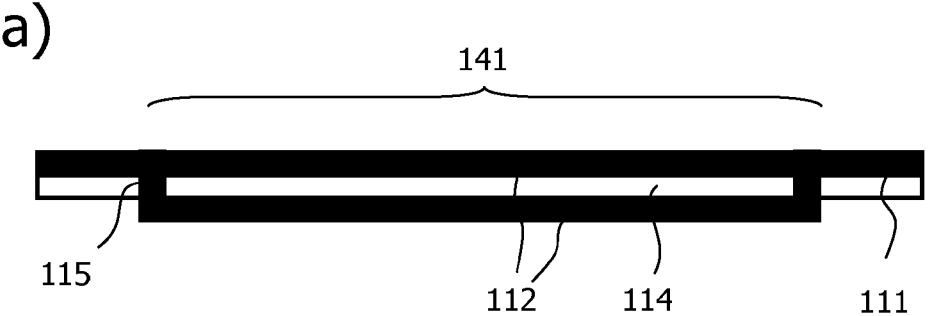
FIG. 13 illustrates the adaptation of resistance in a tuning section by parallel lines of different lengths (topview)
Figure 13:
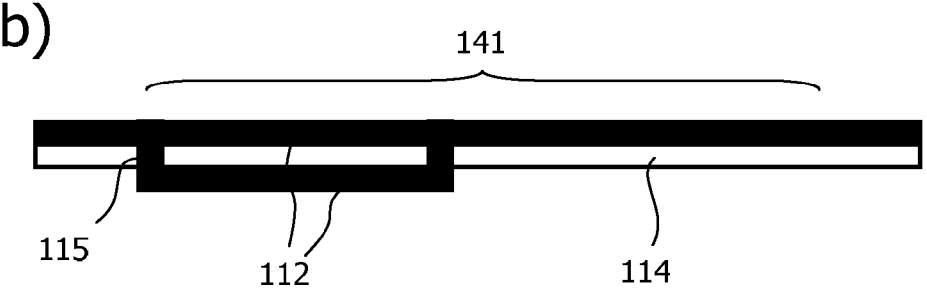

FIG. 13 illustrates another design of a tuning section 141 by "multiple conductive layers". FIGS. 13 a) and 13 b) show cross-sections of the tuning sections 141 of two tracks 111 (the cross sections are taken along the direction of current flow). At least the part of the multichannel tracks within the tuning sections 141 can be made from more than one conductive layer 112, separated by non-conductive material(s) 114. The layers are electrically connected to each other by "vias" 115, i.e. openings in the non-conductive separation layer 114. These conductive layers 112 form parallel resistor circuits, therefore lowering the total resistance of each track in the tuning section 141. The resistance can be tuned by adjusting the length of such parallel resistor circuits. This approach can be particularly useful if such multi-layer structure is already used in the multichannel tracks to reduce total resistance, for instance due to difficulties in achieving a thick layer in single deposition.

Figure 14:
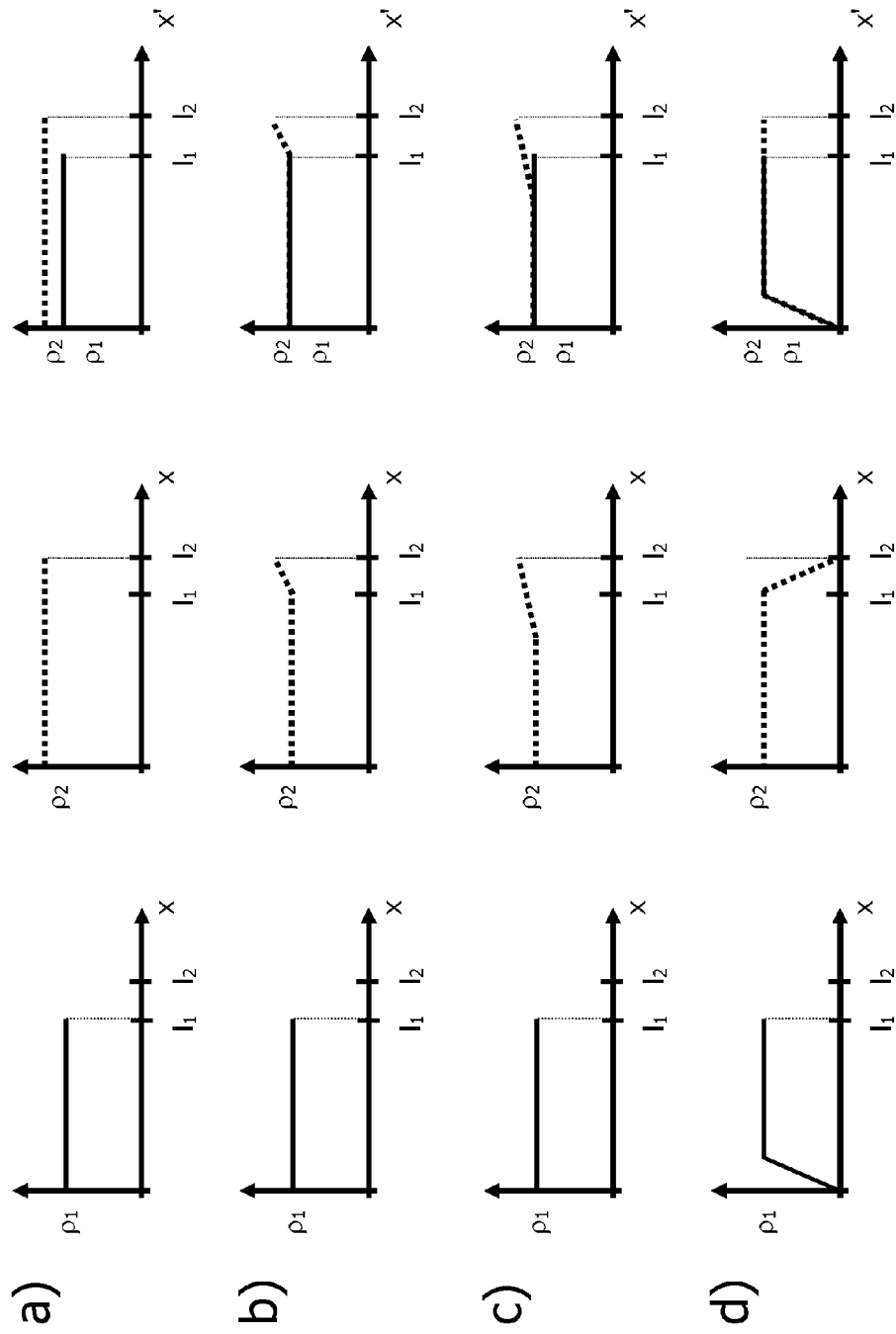
FIG. 14 shows diagrams illustrating non-matching (a, c) and matching (b, d) courses of resistivity.

FIG. 14 illustrates several exemplary cases of courses of resistivity along lines 111, 111' that are matching or non-matching, respectively.

In FIG. 14a, the course of resistivity $\rho_1$ of a first electrical line is shown in the left diagram as a function of position x along said line. In the middle diagram of FIG. 14a, the resistivity $\rho_2$ of a second electrical line is represented accordingly, wherein the length $l_2$ of said second line is assumed to be longer than the length $l_1$ of the first line.

The rightmost diagram of FIG. 14a shows a superposition of the previous two diagrams and clearly illustrates that the two courses of $\rho_1$ and $\rho_2$ are non-matching.

In the example of FIG. 14b, both the first and the second line have the same (constant) resistivity $\rho_1$, $\rho_2$ over the extension $l_1$ of the first line. Accordingly, the courses of resistivity of these two lines are considered to be matching despite the fact that the resistivity $\rho_2$ of the second line differs in the section corresponding to the additional length of this line.

In contrast to this, the courses of resistivity $\rho_1$, $\rho_2$ in FIG. 14c are non-matching because the second resistivity $\rho_2$ starts to deviate from the (constant) value of the first resistivity $\rho_1$ already within the extension $l_1$ of the first line.

Finally, FIG. 14d shows two matching courses of resistivity because the second curve of $\rho_2$ can be brought to an overlap with the first curve of $\rho_1$ along the (smaller) length $l_1$ after mirroring it. This illustrates that the starting-points P1 and end-points P2 of the resistivity curves can be chosen appropriately. Only if none of the possible choices brings the resistivity curves to an overlap, these curves are considered to be non-matching.

While the invention has been illustrated and described in detail in the drawings and foregoing description, such illustration and description are to be considered illustrative or exemplary and not restrictive; the invention is not limited to the disclosed embodiments. The invention can particularly be used in any other multi-channel thin-film-based application where given (e.g. equal) resistances of the channels are desirable. These applications comprise neural implants such as the described DBS system, but also hearing implants, visual implants, or catheters with multiple actuating/sensing units.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An electrical multichannel system, comprising:
    a) a plurality of application components and associated access points;
    b) a multichannel track with a plurality of electrical lines, each line connecting one application component to one access point with a given target resistance and comprising a tuning-section with the following features:
        the tuning-section extends between a starting-point and an end-point;
        a distance between starting-point and end-point is the same for all lines;
        a resistivity and a cross-section are substantially the same for all lines at their starting-point;
        a resistivity and a cross-section are substantially the same for all lines at their end-point;
        the resistances between starting-point and end-point differ between at least one first line and one second line.

2. The electrical multichannel system according to claim 1, characterized in that the geometries of the first line and second line are different in their tuning sections.

3. The electrical multichannel system according to claim 1, characterized in that the first line comprises in the tuning section a subsection composed of at least two materials.

4. The electrical multichannel system according to claim 1, characterized in that the first line and the second line have non-matching courses of resistivity in their tuning sections.

5. An electrical multichannel system according to claim 1, wherein
    the first line is not longer than the second line;
    the first and the second lines have non-matching courses of resistivity ($\rho$).

6. The electrical multichannel system according to claim 5, characterized in that the first line comprises a subsection with a resistivity different from the resistivity at any point of the second line or vice versa.

7. The electrical multichannel system according to claim 5, characterized in that the first line and the second line have different resistivities that are constant along their associated tuning sections.

8. The electrical multichannel system according to claim 5, characterized in that said first line and the second line comprise subsections with differently doped substrates.

9. The electrical multichannel system according to claim 5, characterized in that said first line and the second line comprise subsections with silicides.

10. The electrical multichannel system according to claim 5, characterized in that said first line and the second line have different total lengths outside the tuning sections.

11. The electrical multichannel system according to claim 5, characterized in that the target resistances of all of the plurality of electrical lines are equal to each other.

12. The electrical multichannel system according to claim 5, characterized in that the plurality of electrical lines run along curved parallel paths.

13. The electrical multichannel system according to claim 5, characterized in that the plurality of electrical lines are at least partially realized as thin-film conductors.

14. The electrical multichannel system according to claim 5, characterized in that the application components are implantable electrodes.

15. Neural stimulation and/or recording device, comprising an electrical multichannel system according to claim 1.

* * * * *